US008269827B2

(12) United States Patent
Can et al.

(10) Patent No.: US 8,269,827 B2
(45) Date of Patent: Sep. 18, 2012

(54) SYSTEM AND METHODS FOR MAPPING FLUORESCENT IMAGES INTO A BRIGHT FIELD COLOR SPACE

(75) Inventors: Ali Can, Niskayuna, NY (US); Musodiq O Bello, Niskayuna, NY (US); Michael John Gerdes, Niskayuna, NY (US); Qing Li, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 389 days.

(21) Appl. No.: 12/569,396

(22) Filed: Sep. 29, 2009

(65) Prior Publication Data

US 2011/0074944 A1    Mar. 31, 2011

(51) Int. Cl.
*H04N 7/18*        (2006.01)
*G06K 9/00*        (2006.01)

(52) U.S. Cl. .......................................... 348/79; 382/128
(58) Field of Classification Search ................ 348/79, 348/80; 382/128, 133, 134, 182
See application file for complete search history.

(56) References Cited

U.S. PATENT DOCUMENTS

| 7,483,554 | B2 | 1/2009 | Kotsianti et al. | |
|---|---|---|---|---|
| 2001/0017938 | A1 | 8/2001 | Kerschmann et al. | |
| 2004/0223910 | A1 | 11/2004 | Kiselev et al. | |
| 2009/0238457 | A1* | 9/2009 | Rittscher et al. | 382/171 |
| 2009/0245610 | A1* | 10/2009 | Can et al. | 382/133 |
| 2010/0034791 | A1* | 2/2010 | Lelkes et al. | 424/93.21 |
| 2010/0134605 | A1* | 6/2010 | Demos et al. | 348/65 |
| 2010/0299770 | A1* | 11/2010 | Selkirk et al. | 800/17 |
| 2011/0165566 | A1* | 7/2011 | Wittliff et al. | 435/6.11 |

FOREIGN PATENT DOCUMENTS

| GB | 2434651 | 1/2007 |
|---|---|---|
| WO | WO2008021677 | 2/2008 |
| WO | WO2008021681 | 2/2008 |

OTHER PUBLICATIONS

Buchynska et al., "Immunofluorescence Staining of Paraffin Sections: Creating Dab Staining Like Virtual Digital Images Using Cmyk Color Conversion", Experimental Oncology, vol. 30, No. 4, pp. 327-329, Dec. 2008.
Mansfield, James R., "Visualization of Microscopy-Based Spectral Imaging Data from Multi-Label Tissue Sections", Current Protocols in M9leclar Biology 14.19. 1-14, 19, 15, Oct. 2008.
U.S. Appl. No. 11/500,028, filed Aug. 7, 2006, p. 1.
U.S. Appl. No. 11/606,582, filed Nov. 30, 2006, p. 1.
U.S. Appl. No. 11/680,063, filed Feb. 28, 2007, p. 1.
U.S. Appl. No. 11/686,649, filed Mar. 15, 2007, p. 1.

* cited by examiner

*Primary Examiner* — Haresh N Patel
(74) *Attorney, Agent, or Firm* — Eileen W. Gallagher

(57) ABSTRACT

A method for generating a brightfield type image, which resembles a brightfield staining protocol of a biological sample, using fluorescent images is provided. The steps comprise acquiring two or more fluorescent images of a fixed area on a biological sample, mapping said fluorescent image into a brightfield color space, and generating a bright field image. Also provided is an image analysis system for generating a brightfield type image of a biological sample using fluorescent images.

12 Claims, 4 Drawing Sheets

SYSTEM AND METHODS FOR MAPPING FLUORESCENT IMAGES INTO A BRIGHT FIELD COLOR SPACE

BACKGROUND

The invention relates generally to a method to map a set of biomarker images acquired by a fluorescent microscope into a new color space where the mapped image intensity values represent a brightfield modality.

In traditional histological staining with Hematoxylin & Eosin (H&E), the basophilic dye Hematoxylin (H) is used to stain the cell nuclei blue, and the acidophilic dye Eosin (E) is used as a counter-stain to stain cytoplasm, connective tissue (collagen), muscle fibers, connective tissue, and red blood cells. Eosin interacts with different cellular components in the tissue producing different shades of pink color based on charge properties of the molecules to which eosin is binding. These cellular components can be alternatively labeled using molecular markers (dyes and antibodies) with fluorescent dyes. For example, cell nuclei can be stained with DAPI (a fluorescent dye that binds DNA specifically) while other regions in the tissue can be labeled immunofluorescently where the molecules of interest are targeted by directly conjugated antibodies, or by primary secondary amplification detection. For some structures, such as red blood cells (RBC), tissue autofluorescence captured by a set of filters can be used for detection. Fluorescent imaging modality has the advantage of capturing each of these tissue structures individually, hence enabling accurate localization and quantification.

However, histopathological diagnosis based on fluorescent images is not a common practice because fluorescent images do not provide structural and morphological details that are essential for pathologists to diagnose. Brightfield H&E staining techniques are also often favored because there exists a large body of knowledge about these techniques, assembled for decades in pathology laboratories.

A method of transforming fluorescent images into a color domain that resembles brightfield images, such as H&E is desirable to allow pathologists to perform both quantitative analysis as well as pathologic diagnostics on the same set of fluorescent images.

BRIEF DESCRIPTION

As noted, fluorescent markers were previously used alone to identify the nuclei, epithelia and stroma to provide information on the cell compartments. The methods combine the morphological function of fluorescent markers with the function of fluorescent biomarkers, which are used to identify the expression of proteins and pathways for disease in tissue based, in part, on cell morphology and biological pathways. The disclosed invention describes a method to map a set of biomarker and autofluorescence images acquired by a fluorescent microscope into a new color space where the mapped image intensity values represent a brightfield modality such as H&E staining.

In one embodiment, a method for generating a brightfield type image, that resembles a brightfield staining protocol of a biological sample, using fluorescent images is provided for. The method comprises the steps of acquiring two or more fluorescent images of a fixed area on a biological sample, mapping said fluorescent image into a brightfield color space, and generating a bright field image.

In another embodiment an image analysis system for generating a brightfield type image, that resembles a brightfield staining protocol of a biological sample, using fluorescent images is provided. The system comprises a digital imaging device adapted to acquire two or more fluorescent images of a fixed area on a biological sample, and a processing device adapted to apply mapping parameters to transform the two or more fluorescent images into a brightfield type image.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
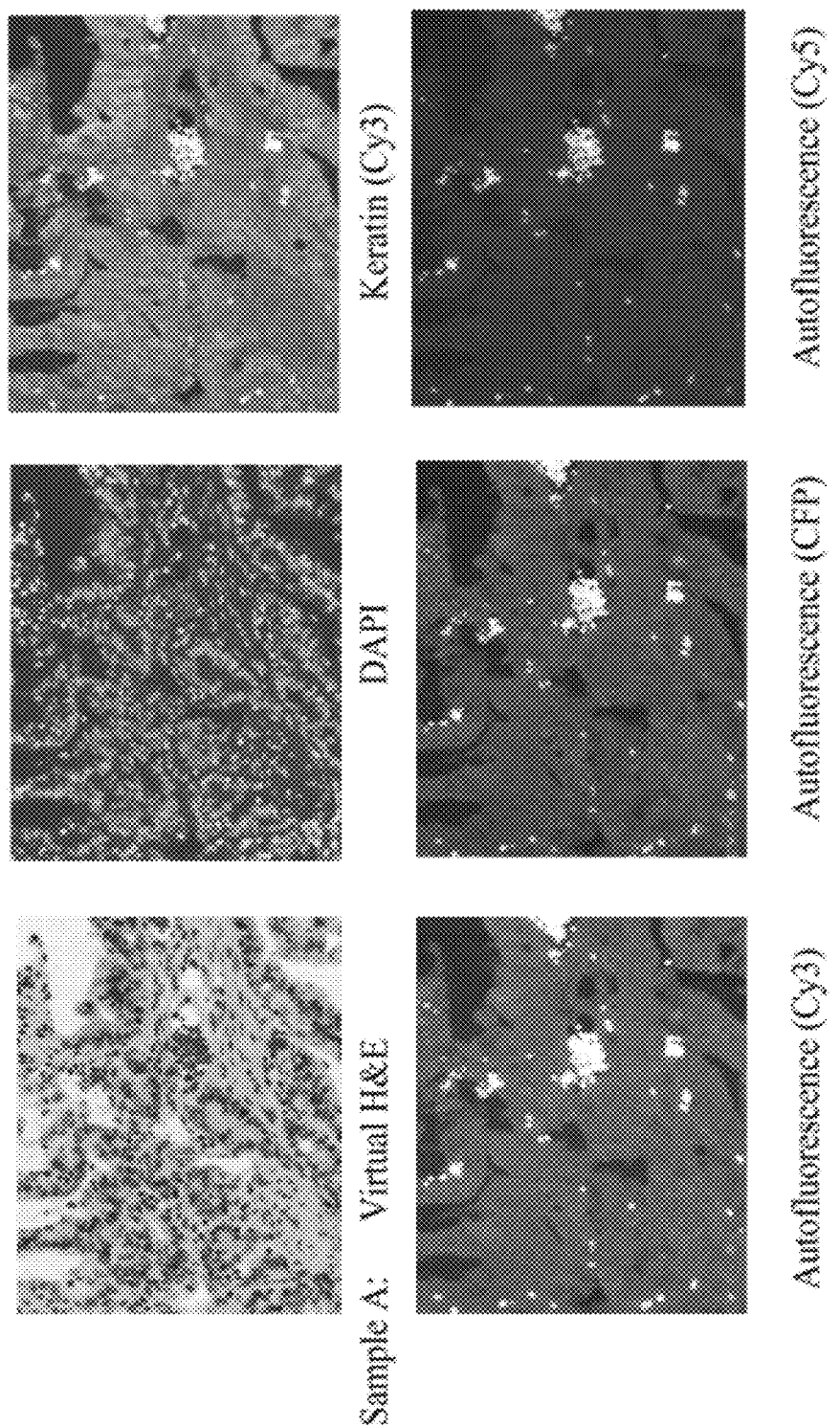
FIG. 1 shows a monochromatic embodiment of 5 fluorescent images of a colon tissue sample (sample A) and the corresponding generated H&E type image.

To more clearly and concisely describe and point out the subject matter of the claimed invention, the following definitions are provided for specific terms that are used in the following description and the claims appended hereto.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')2, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythro sine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC, (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes, and squaraines.

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker, which may include a cleavage site) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators include one or more of a chromophore, a fluorophore, a Raman-active tag, or a radioactive label. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about 105 M$^{-1}$ under ambient conditions such as a pH of about 6 to about 8 and temperature ranging from about 0° C. to about 37° C.

As used herein, the term "target," refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

As used herein the term "virtual stained image" (VSI) refers to an image of a biological sample that simulates that of an image obtained from a brightfield staining protocol. The image has similar contrast, intensity, and coloring as a brightfield image. This allows features within a biological sample, including but not limited to nuclei, epithelia, stroma or any type of extracellular matrix material features, to be characterized as if the brightfield staining protocol was used directly on the biological sample.

The invention includes embodiments that relate generally to methods applicable in analytical, diagnostic, or prognostic applications such as analyte detection, histochemistry, immunohistochemistry, or immunofluorescence. In some embodiments, the methods disclosed herein may be particularly applicable in histochemistry, immunostaining, immunohistochemistry, immunoassays, or immunofluorescence. In some embodiments, the methods disclosed herein may be particularly applicable in immunoblotting techniques, for example, western blots or immunoassays such as enzyme-linked immunosorbent assays (ELISA).

Methods for sequential staining and detecting multiple targets in a biological sample is described more fully in U.S. patent application Ser. No. 11/864,085 entitled "Sequential Analysis of Biological Samples", filed on Sep. 28, 2007 is incorporated herein by reference. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel Images of a Tissue Micro Array", filed on Aug. 7, 2006; U.S. patent application Ser. No. 11/606,582, entitled "System and Methods for Scoring Images of a Tissue Micro Array, filed on Nov. 30, 2006, and U.S. application Ser. No. 11/680,063, entitled Automated Segmentation of Image Structures, filed on Feb. 28, 2007, each of which is herein incorporated by reference.

Methods to convert fluorescent images into a pseudo brightfield image are known. However, these methods typically reassign a specific color space (wavelength) to each fluorescent dye such that the fluorescent images are recolored into the brightfield space. These methods do not transpose the fluorescent images into an image that represents the image of the biological sample that would be obtained if the biological sample were subjected to a specified brightfield staining protocol, such as H&E. In contrast the invention described herein, creates a brightfield image from fluorescent images wherein structural features and details of the biological sample are identified as if the image was obtained directly from a specified brightfield staining protocol. The images that resemble the brightfield staining protocol may be referred to as a virtual stained image (VSI).

The disclosed invention describes a method to map a set of biomarker images acquired by a fluorescent microscope into a new color space where the mapped image intensity values represent a brightfield modality and may be used to generate a VSI. The method involves using data acquired from corresponding points in two or more fluorescent images and a bright-field image of a biological sample. The data is used to estimate an unknown intensity transformation that maps the fluorescent images into the brightfield color space using estimated mapping parameters $\hat{A}$.

In embodiments wherein the brightfield color space is obtained using H&E morphological stain, $\hat{A}$ may be defined as:

$$\hat{A} = \arg\min_{A} (HE - A \cdot FL)^2$$

where A is the unknown mapping parameters, and HE and FL represent matrices that store the known set of corresponding H&E and fluorescent pixels, respectively. More specifically, HE represents intensity values in the color channels of the H&E image and FL is the intensity values of at least one of the fluorescent markers or autofluorescence at the corresponding point in the fluorescent image color space. The estimated mapping parameter may be calculated using a variety of regression analysis models including, but not limited to, ordinary linear least squares (OLS), generalized least squares (GLS), iteratively reweighted least squares (IRLS), or orthogonal estimation methods.

In embodiments wherein a linear least square estimation is used $\hat{A}$ may be further calculated by:

$\hat{A} = (HE \cdot FL^T)(FL \cdot FL^T)^{-1}$ where $FL^T$ is the transpose of the FL matrix, and (−1) represent the matrix inversion.

The correspondence of the points in the fluorescent images and the bright-field images, which were used to calculate the mapping parameters, may be established by two methods: intensity-based and feature-based.

In a feature-based method, the image of the nuclei, epithelia, stroma or any type of extracellular matrix material is acquired for both the fluorescent image and the bright-field image. The featured-based structure may be selected using a manual process or automatically. Corresponding structures are selected in images from both modalities. For the fluorescent image, the image may be captured using a fluorescent microscope with an appropriate excitation energy source tuned to a given biomarker and with filters appropriate for collecting the emitted light. Similarly, multiple biomarkers can be imaged simultaneously without moving the sample under the microscope, or sequentially. As noted, the excitation wavelength and the filters can be changed for different markers. In certain embodiments, the microscope may be designed so that it can acquire both bright field and fluorescent images. One such microscope may involve calibrated multiple optical paths and multiple cameras. A bright field image of the sample may then be obtained which may then be segmented into Red (R), Green (G) and Blue (B) channels and the color and intensity of the feature-based structure measured.

In an intensity-based method, location of the sample area under the microscope may be controlled with electronic, magnetic, optical or mechanical sensors so that the sample area can be repeatedly located close to the same position for the next image acquisition. Intensity based registration is generally applicable to a broad class of biomarkers. Generally, the biological sample, which is fixed or otherwise provided on a substrate such as, but not limited to, a TMA, a slide, a well, or a grid, is labeled with molecular biomarkers, and imaged through a fluorescent microscope.

In one embodiment, a variety of molecular biomarkers may be used such as fluorescent dyes bound to antibodies or proteins. Then the sample is imaged under a fluorescent microscope using an excitation energy source that is tuned to the given biomarkers, and using various filters that are adapted to optimally collect the emitted light. Multiple biomarkers can be imaged simultaneously without moving the specimen under the microscope, or sequentially. For different biomarkers the excitation wavelength and the filters can be changed. Biomarkers may include, but are not limited to, the following list of markers which comprises a brief description of one or more but not necessarily all of the functions of each marker:

Her2/neu: epidermal growth factor over expressed in breast and stomach cancer, therapy by a monoclonal antibody slows tumor growth EGF-R/erbB: epidermal growth factor receptor ER: estrogen receptor required for growth of some breast cancer tumors, located in the nucleus and detected with ISH for deciding on therapy limiting estrogen in positive patients PR: progesterone receptor is a hormone that binds to DNA AR: androgen receptor is involved in androgen dependant tumor growth P53: tumor suppressor gene senses DNA damage; is inactivated in 50% of human cancer β-catenin: oncogene in cancer translocates from the cell membrane to the nucleus, which functions in both cell adhesion and as a latent gene regulatory protein Phospho-γ-Catenin: phosphorylated form of β-catenin degrades in the cytosol and does not translocate to the nucleus GSK3β: glycogen synthase kinase-3β protein in the Wnt pathway phosphorylates β-catenin marking the phospho-β-catenin for rapid degradation in the protosomes PKCβ: mediator G-protein coupled receptor NFKβ: nuclear factor kappa B marker for inflammation when translocated to the nucleus Bcl-2: B cell lymphoma oncogene 2 acts as an apoptosis inhibitor CyclinD: cell cycle control VEGF: vascular endothelial growth factor related to angiogenesis E-cadherin: cell to cell interaction molecule expressed on epithelial cells, the function is lost in epithelial cancers c-met: tyrosine kinase receptor.

At least one additional fluorescent morphological marker that carries compartmental information may also be included in this step. This marker is chosen such that it carries common information with the next step and is used to register the images if sequential staining is involved. An area of the biological sample is then re-labeled with one or more morphological markers, which are visible in the brightfield color space, such as hematoxylin and eosin (H&E) dyes, and imaged again.

In some embodiments morphological markers may include, but are not limited to, the following:

Keratin: marker for epithelial cells

Pan-cadherin: marker for the cell membrane

Smooth muscle actin: marker for muscle

DAPI: marker for the nucleus

Hematoxylin marker for DNA (blue stain)

Eosin: marker for cytoplasm; depends on pH (red stain).

Some of these morphological markers can be imaged using a brightfield microscope, and some with fluorescent microscope. In any case, the morphological marker is chosen such that it has common information with the earlier step. For example if DAPI is used to image the nuclei in the earlier step, hematoxylin can be used to image the nuclei under a bright field microscope in the second step. Since they both stain the same compartment, the images can be aligned by image registration techniques. DAPI a nuclear stain may be employed as the additional fluorescent morphological marker to register the nucleus stained with hematoxylin in the bright-field images with the fluorescent images. The images of the sample area are overlaid using both hardware and software registration techniques, and the information is stored whereby the technical effect is to register or otherwise produce multichannel images of the sample area.

An intensity-based method therefore allows both molecular and morphological markers to be imaged from the same biological sample using sequential imaging and co-registration techniques. Subsequently, the pixel intensity for given points on the area of the biological sample may be registered and compared for both the fluorescent images and the brightfield image. Similar to the feature-based method, the brightfield image is segmented into Red (R), Green (G) and Blue (B) channels.

In either the intensity-based or feature-based method, the transformation from the fluorescent images to the brightfield color space uses the estimated mapping parameter Â in a linear transformation equation. The linear transformation equation may be represented as HE=Â·FL, when using H&E dyes, or in the matrix notation as:

$$\begin{bmatrix} HE_{RED} \\ HE_{GREEN} \\ HE_{BLUE} \end{bmatrix} = \begin{bmatrix} a_{1,1} & a_{1,2} & \ldots & a_{1,N} & a_{1,N+1} \\ a_{2,1} & a_{2,2} & \ldots & a_{2,N} & a_{2,N+1} \\ a_{3,1} & a_{3,2} & \ldots & a_{3,N} & a_{3,N+1} \end{bmatrix} \begin{bmatrix} FL_1 \\ FL_2 \\ \vdots \\ FL_N \\ 1 \end{bmatrix}$$

where "a" represents the unknown transformation parameters that needs to be estimated. Using the matrix notation, the brightfield image is segmented into a RGB color channel and the number of fluorescent channels is application specific and based on how many compartments and protein associations are needed for the specific task. The last row of the FL matrix comprises a row of 1's to model the constant terms in the mapping. Usually three or four fluorescent dyes can be easily applied simultaneously, however more may be used. For example, if there are 100 feature points and the fluorescent images comprise four different markers, then the size of FL matrix is 5×100, the size of matrix A is 3×5, and the size of HE matrix is 3×100.

Once the transformation parameters are calculated, one or more selected areas of the sample may be used for transformation from a set of fluorescent images into a VSI using the virtual H&E mapping. The molecular biomarkers advantageously provide functional and compartmental information that is not visible using a brightfield image alone. For example, image analysis algorithms can benefit from the added channels to separate the sample compartments while still providing a pathologist or operator an image intensity values representative of a brightfield modality (H&E). For example a VSI representative of a H&E staining protocol would show blood cells as red, nuclei as purple, and connective tissue as pink.

In other embodiments, once the mapping parameters are estimated, the transformation algorithm may be applied to other fluorescent images to generate a VSI. The other fluorescent images may be from a different area of the same biological sample. For example, the source of the biological sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In other embodiments, the other fluorescent images used to generate a VSI may be from a different biological sample. The different biological sample may include a collection of similar cells obtained from tissues of biological subjects that may have a similar function. Suitable examples of human tissues include, but are not limited to, (1) epithelium; (2) the connective tissues, including blood vessels, bone and cartilage; (3) muscle tissue; and (4) nerve tissue.

In some embodiments, a biological sample includes tissue sections from healthy or diseases tissue samples (e.g., tissue section from colon, breast tissue, prostate). A tissue section may include a single part or piece of a tissue sample, for example, a thin slice of tissue or cells cut from a tissue sample. In some embodiments, multiple sections of tissue samples may be taken and subjected to analysis.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

In certain embodiments, the VSI generated may be used for pathological diagnostics and may further comprise the step of identifying one or more molecular pathways based on the molecular marker, wherein the molecular pathway is indicative of a disease. Although the methods may be used for a variety of diseases, one type for which the method is particularly suited is cancer including, but not limited to, epithelial cancers such as but not limited to breast, prostate and colon cancers.

In certain embodiments, the VSI generated may be used for quantitavie analysis comprising identifying molecular pathways as a function of one or more morphological structures selected from a group consisting of nuclei, epithelia, and stroma. For example, a stained fluorescent image may be transformed to an H&E coordinate system and viewed together to provide enhanced analysis.

An image analysis system for carrying out the method generally comprises: a means for at least temporarily storing the digital images stained with the molecular markers and the morphological stains in both the fluorecent and brightfield spaces; and a processor for co-registering the images using one or more registration if sequential staining is involved. The processor is also configured to calculate the mapping parameters by analyzing at least in part, featured based information or pixel intensity data information of the bright field image and the two or more fluorescent images to transform the two or more fluorescent images into a VSI.

The system may further comprise a means for displaying one or more of the images; an interactive viewer; a virtual microscope; and/or a means for transmitting one or more of the images over a communications network. The processor may also superimpose one or more of the images with each other based, at least in part, on the segmentation of the morphological features.

In certain embodiments the processor is also configured to store mapping parameters from one or more previously analyzed biological samples. This provides a means for applying the transformation algorithm to other fluorescent images to generate a VSI. The other fluorescent images may be from a different area of the same biological sample or from different biological samples. The system may also allow the user to select from many available transformations and even adjust the transformation parameters interactively based on a visual inspection of the expected output (generated VSI).

In some embodiments, one or more of the aforementioned may be automated and may be performed using automated systems. In some embodiments, all the steps may be performed using automated systems.

EXAMPLE

Comparison of H&E Images for Colon Tissue Samples

Adult human colon tissue samples (Biochain, T2234090) were obtained as tissue slides embedded in paraffin. Paraffin embedded slides, of adult human tissue, were subjected to an immunohistochemistry protocol to prepare them for staining. The protocol included deparaffinization, rehydration, incubation, and wash. Deparaffinization was carried by washing the slides with Histochoice (or toluene) for a period of 10 minutes and with frequent agitation. After deparaffinization, the tissue sample was rehydrated by washing the slide with ethanol solution. Washing was carried out with three different solutions of ethanol with decreasing concentrations. The concentrations of ethanol used were 90 volume %, 70 volume %, and 50 volume %. The slide was then washed with a phosphate buffer saline (PBS, pH 7.4). Membrane permeabilization of the tissue was carried out by washing the slide with 0.1 weight percent solution of Triton TX-100. Citrate buffer pH 6.0 (Vector Unmasking Solution) was used for antigen retrieval. The slides were exposed to the buffer in a pressure cooker for a period of 15 minutes followed by cooling at room temperature for 20 minutes. The slide was then blocked against non-specific binding by washing with PBS and 900 µL of 3 volume percent bovine serum albumin (BSA) for 45 minutes at 37° C. For staining with secondary antibodies (optional), the slide was also blocked with 100 µL of serum from secondary antibody host species.

Figure 2:
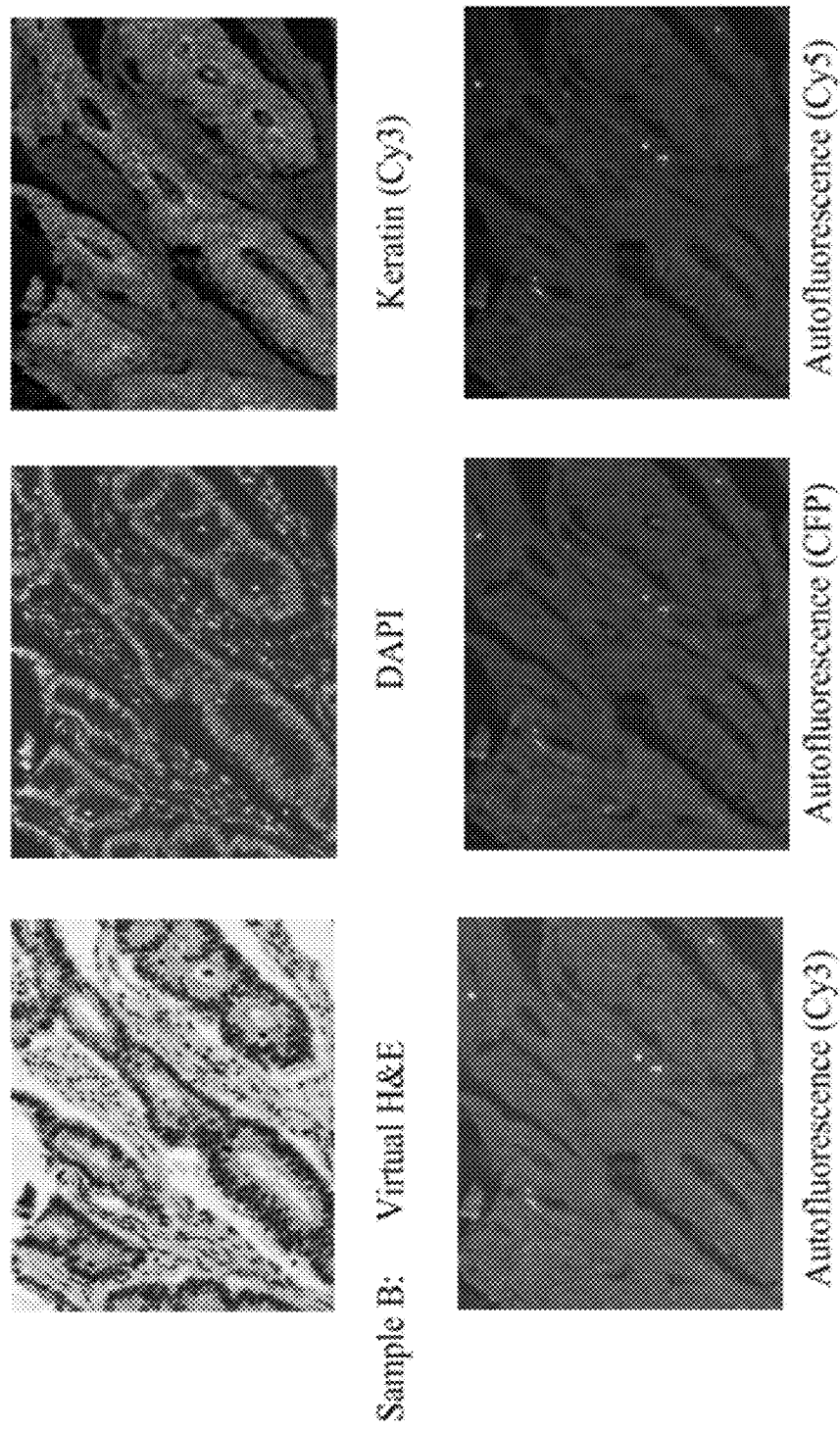
FIG. 2 shows a monochromatic embodiment of 5 fluorescent images of a colon tissue sample (sample B) and the corresponding generated H&E type image.

The colon slides prepared was stained and imaged using procedures described in U.S. patent application Ser. No. entitled "Sequential Analysis of Biological Samples". To generate five fluoroecent images including: DAPI, Keratin (Cy3), Autofluorecence (Cy3), Autofluorecence (CFP) and Autofluorecence (Cy5) as shown in FIG. 1 and FIG. 2. FIG. 1 and FIG. 2 represent images obtained from different colon tissue samples (samples A and B for reference). In general staining and imaging of the colon slide included incubation with a dye-conjugated antibody in 3 percent BSA for 45 minutes at 37° C. After incubation, the slide was subjected to an extensive series of PBS washes. The slide was incubated with a secondary antibody in BSA for 45 minutes at 37° C. After incubation, the slide was subjected to an extensive series of PBS washes. A primary antibody or secondary antibody-stained slide was counterstained with the morphological stain, DAPI, and cover slipped.

A cover slipped slide was imaged using a camera. The camera used was a monochromatic Leica DFC 350FX monochromatic high-resolution camera mounted in a Leica DMRA2 fluorescent microscope. The magnification used was 20× unless otherwise stated. After image acquisition, the cover slip was removed and the slide was washed with PBS to prepare for signal destruction.

FIGS. 1 and 2 also shows a micrograph of a generated H&E type image using estimated mapping parameters. FIG. 1 shows a monochromatic embodiment of 5 fluorescent images of a colon tissue sample and the corresponding generated H&E type image (VSI, sample A). FIG. 2 shows a monochromatic embodiment of 5 fluorescent images of a colon tissue sample and the corresponding generated H&E type image (VSI, sample B).

A set of corresponding points are identified manually for an H&E image and a set of fluorescent images comprised of a DAPI image, a membrane marker image, and three fluorescent images taken using Cy3, Cy5, and CFP filter cubes. The fluorescent images are normalized such that the minimum value is set to zero and the maximum value is set to one. Furthermore the normalized fluorescent images are inverted so that the background is bright and the foreground is dark. The three channels of the autofluorescent images are very correlated. All the autofluorescent images can be geometrically, and algebraically averaged to produce two new images that can be used in the mapping. The estimated transformation matrix for this sample dataset is:

$$\hat{A} = \begin{bmatrix} 0.86 & 0.00 & 0.00 & 0.10 & -0.62 \\ 1.05 & 0.30 & 0.19 & 0.58 & -3.10 \\ 0.34 & 0.16 & 0.04 & 0.12 & -0.09 \end{bmatrix}$$

Figure 3:
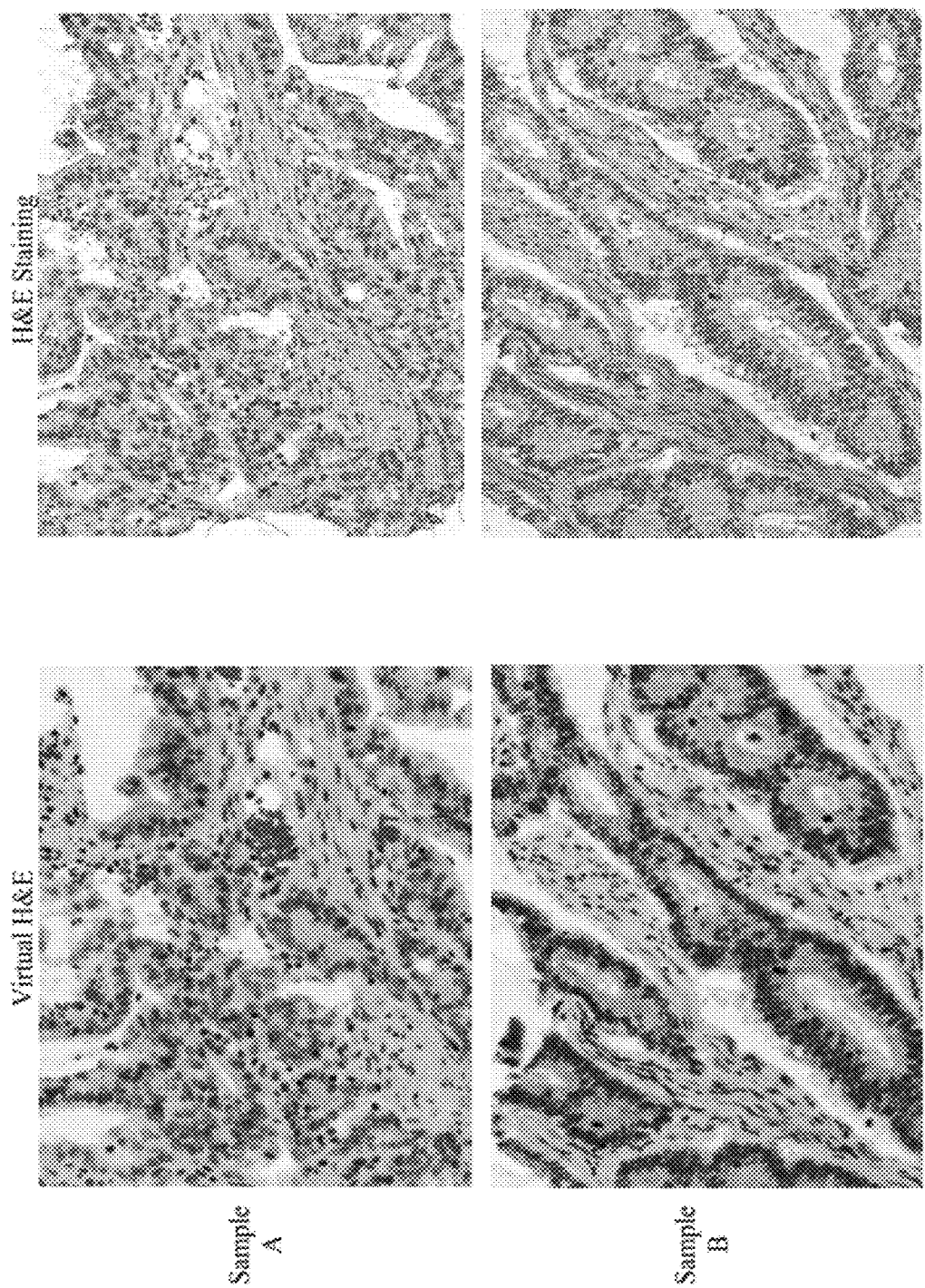
FIG. 3 shows a monochromatic embodiment of a three-channel (red, green, blue) color image of a H&E stained colon tissues compared to H&E type images generated from fluorescent images

After fluorescent imaging, the slide was stained with morphological stains H&E and an image acquired using a brightfield setting. The images for both sample A and sample B are shown in FIG. 3 along with the generated VSI from FIG. 1 and FIG. 2.

These methods merge molecular pathology and standard anatomical pathology. H&E based staining is the most common bright field microscopy staining technique used in standard pathology. As described above, hematoxylin stains cell nuclei blue, while, as a counter-stain, eosin stains cytoplasm and connective tissue pink. There are a great number of other known stain combinations that can be used as alternative staining for bright field microscopy. For example, Feulgen staining can be used to image nucleic acids, or Orcein can be used to image connective tissue fibers.

These multi-channel methods are not limited to morphological stains or fluorescent biomarkers or even to pathology. Any stain that enables some informative aspect or feature of a biological sample to be visualized so that it can be digitally imaged and processed would be suitable for these methods. Suitable stains include, but are not necessarily limited to, cytological or morphological stains, immunological stains such as immunohisto- and immunocyto-chemistry stains, cytogenetical stains, in situ hybridization stains, cytochemical stains, DNA and chromosome markers, and substrate binding assay stains. Other medical and bioscience applications can benefit from the extended multi-channels. These multi-channel methods provide a flexible framework in which markers can be imaged sequentially without being limited to optical, chemical, and biological interactions.

Figure 4:
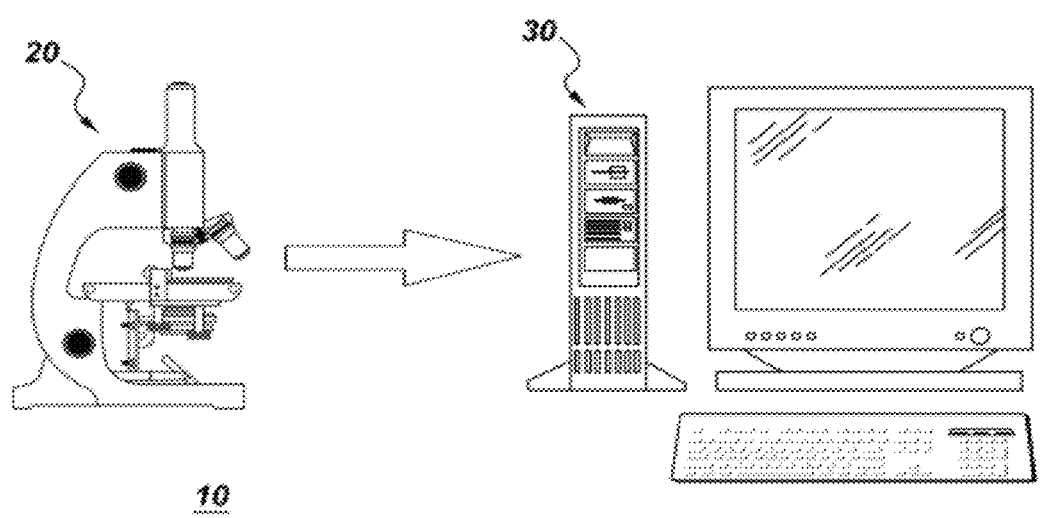
FIG. 4 shows a schematic diagram of a representative image analysis system for mapping fluorescent images into a bright field color space.

FIG. 4 is a schematic diagram of a representative image analysis system (10) for mapping fluorescent images into a bright field color space. The system (10) comprises a digital imaging device (20) to acquire two or more fluorescent images of a sample and a processing device (30) for apply mapping parameters to transform the fluorescent images into a brightfield type image.

While only certain features of the invention have been illustrated and described herein, many modifications and changes will occur to those skilled in the art. It is, therefore, to be understood that the appended claims are intended to cover all such modifications and changes as fall within the scope and spirit of the invention.

We claim:

1. A method for generating a brightfield type image, that resembles a brightfield staining protocol of a biological sample, using fluorescent images comprising the steps of:
   acquiring, by a digital imaging device, two or more fluorescent images of a fixed area on a biological sample;
   mapping said fluorescent images into a brightfield color space; and
   generating a bright field type image;
   the mapping step comprises:
      acquiring a bright field image of the fixed area of the biological sample;
      analyzing the image data of the bright field image and the two or more fluorescent images utilizing, at least in part, featured based information or pixel intensity data information to generate mapping parameters to transform the two or more fluorescent images into a bright field color space; and
      applying said mapping parameters to the two or more fluorescent images;
   the generating mapping parameters step comprises:
      using a linear estimation model;
   the linear estimation model is defined as:

$$\hat{A} = \arg\min_{A} \ (HE - A \cdot FL)^2$$

where $\hat{A}$ is the estimated mapping parameters, HE represents intensity values in the color channels of the Hematoxylin & Eosin (H&E) image, and FL is the intensity values of at least two color channels of the fluorescent images.

2. The method of claim 1 wherein the brightfield type image corresponds to an Hematoxylin & Eosin (H&E) type image having a red, green, and blue three channel color space.

3. The method of claim 1 wherein at least one image of the two or more fluorescent images is of autofluorescence.

4. The method of claim 1 wherein the acquiring a bright field image step comprises the steps of sequentially staining the biological sample with hematoxylin and eosin to generate an Hematoxylin & Eosin (H&E) type image.

5. The method of claim 1 wherein the feature based information comprises one or more features selected from a group consisting of nuclei, epithelia, and stroma.

6. The method of claim 1 further comprising the step of applying the mapping parameters to two or more fluorescent images of a second fixed area wherein the second fixed area is from the same or a different biological sample.

7. The method of claim 1 further comprising the step of pathological diagnostics using said brightfield type image.

8. The method of claim 7 wherein the pathological diagnostics is for cancer.

9. The method of claim 1 further comprising the step of quantitative analysis using said brightfield type image.

10. The method of claim 9 wherein the step of quantitative analysis comprises identifying molecular pathways as a function of one or more morphological structures selected from a group consisting of nuclei, epithelia, and stroma.

11. An image analysis system for generating a brightfield type image, that resembles a brightfield staining protocol of a biological sample, using fluorescent images comprising:
a digital imaging device to acquire two or more fluorescent images of a fixed area on a biological sample; and
a processing device to apply mapping parameters to transform the two or more fluorescent images into a brightfield type image;
the processing device is to calculate the mapping parameters by:
acquiring a bright field image of the fixed area of the biological sample;
analyzing at least in part, feature based information or pixel intensity data information of the bright field image and the two or more fluorescent images to transform the two or more fluorescent images into a bright field color space;
the analyzing step comprises a linear estimation model;
the linear estimation model is defined as:

$$\hat{A} = \arg\min_{A}(HE - A \cdot FL)^2$$

where $\hat{A}$ is the estimated mapping parameters, HE represents intensity values in the color channels of the Hematoxylin & Eosin (H&E) image, and FL is the intensity values of at least two color channels of the fluorescent images.

12. The system of claim 11 wherein the processing device is further configured to store mapping parameters from one or more previously analyzed biological samples.

* * * * *